(12) United States Patent
Davison et al.

(10) Patent No.: US 8,177,783 B2
(45) Date of Patent: May 15, 2012

(54) ELECTRIC PLASMA-MEDIATED CUTTING AND COAGULATION OF TISSUE AND SURGICAL APPARATUS

(75) Inventors: Paul O. Davison, Montara, CA (US); Daniel V. Palanker, Sunnyvale, CA (US); Alexander B. Vankov, Menlo Park, CA (US)

(73) Assignee: Peak Surgical, Inc., Palo Alto, CA (US)

( * ) Notice: Subject to any disclaimer, the term of this patent is extended or adjusted under 35 U.S.C. 154(b) by 1230 days.

(21) Appl. No.: 11/982,734

(22) Filed: Nov. 1, 2007

(65) Prior Publication Data
US 2008/0140066 A1 Jun. 12, 2008

Related U.S. Application Data (60) Provisional application No. 60/856,549, filed on Nov. 2, 2006.

(51) Int. Cl.
*A61B 18/14* (2006.01)
(52) U.S. Cl. .............. 606/37; 606/41; 606/45
(58) Field of Classification Search ........... 606/32–48
See application file for complete search history.

(56) References Cited

U.S. PATENT DOCUMENTS

| | | | |
|---|---|---|---|
| 3,799,168 A | 3/1974 | Peters | |
| 3,903,891 A | 9/1975 | Brayshaw | |
| 3,970,088 A | 7/1976 | Morrison | |
| 3,987,795 A | 10/1976 | Morrison | |
| 4,034,762 A | 7/1977 | Cosens et al. | |
| 4,043,342 A | 8/1977 | Morrison, Jr. | |
| 4,074,718 A | 2/1978 | Morrison, Jr. | |
| 4,161,950 A | 7/1979 | Doss et al. | |
| 4,202,337 A | 5/1980 | Hren et al. | |
| 4,211,230 A | 7/1980 | Woltosz | |
| 4,228,800 A | 10/1980 | Degler, Jr. et al. | |
| 4,248,231 A | 2/1981 | Herczog et al. | |

(Continued)

FOREIGN PATENT DOCUMENTS
EP 0 012 037 A1 6/1980
(Continued)

OTHER PUBLICATIONS
International Preliminary Report on Patentability mailed on May 14, 2009, for PCT Application No. PCT/US2007/023130, filed on Nov. 1, 2007, seven pages.
(Continued)

*Primary Examiner* — Linda Dvorak
*Assistant Examiner* — Amanda Scott
(74) *Attorney, Agent, or Firm* — Morrison & Foerster LLP (57) ABSTRACT

Electrosurgery method and apparatus. In the method, tissue is cut or coagulated, with an electrically low conductive liquid providing cooling. In another method, skin is cut by electrosurgery in a dry field using a low duty cycle signal energizing the cutting electrode, minimizing tissue charring. A combination coagulation and cutting electrode performs both functions. The cutting is performed by a blade edge generating a local plasma adapted for cutting. Superimposed on the blade edge is an electrode of greater surface area electrically insulated from the cutting electrode, for coagulation. In another version, a single component cutting/coagulation blade (electrode) has a cutting and a flat partially insulated portion defining through holes in the insulation for coagulation. Also provided is an electrical circuit whereby each electrode is isolated by a filter from cross talk and feedback of the RF signal from the other electrode, minimizing arcing.

7 Claims, 5 Drawing Sheets

U.S. PATENT DOCUMENTS

| | | |
|---|---|---|
| 4,429,694 A | 2/1984 | McGreevy |
| 4,438,766 A | 3/1984 | Bowers |
| 4,473,075 A | 9/1984 | Rexroth |
| 4,476,862 A | 10/1984 | Pao |
| 4,492,231 A | 1/1985 | Auth |
| 4,534,347 A | 8/1985 | Taylor |
| 4,559,943 A | 12/1985 | Bowers |
| 4,589,411 A | 5/1986 | Friedman |
| 4,590,934 A | 5/1986 | Malis et al. |
| 4,593,691 A | 6/1986 | Lindstrom et al. |
| 4,597,388 A | 7/1986 | Koziol et al. |
| 4,655,215 A | 4/1987 | Pike |
| 4,674,498 A | 6/1987 | Stasz |
| 4,674,499 A | 6/1987 | Pao |
| 4,682,596 A | 7/1987 | Bales et al. |
| 4,781,175 A | 11/1988 | McGreevy et al. |
| 4,805,616 A | 2/1989 | Pao |
| 4,901,709 A | 2/1990 | Rattner et al. |
| 4,927,420 A | 5/1990 | Newkirk et al. |
| 4,936,301 A | 6/1990 | Rexroth et al. |
| 4,938,761 A | 7/1990 | Enssllin |
| 4,943,290 A | 7/1990 | Rexroth et al. |
| 5,080,660 A | 1/1992 | Buelna |
| 5,088,997 A | 2/1992 | Delahuerga et al. |
| 5,108,391 A | 4/1992 | Flachenecker et al. |
| RE33,925 E | 5/1992 | Bales et al. |
| 5,151,102 A | 9/1992 | Kamiyama et al. |
| 5,217,457 A | 6/1993 | Delahuerga et al. |
| 5,254,121 A | 10/1993 | Manevitz et al. |
| 5,267,994 A | 12/1993 | Gentelia et al. |
| 5,267,998 A | 12/1993 | Hagen |
| 5,281,216 A | 1/1994 | Klicek |
| 5,300,068 A | 4/1994 | Rosar et al. |
| 5,318,563 A | 6/1994 | Malis et al. |
| 5,348,553 A | 9/1994 | Whitney |
| 5,423,814 A | 6/1995 | Zhu et al. |
| 5,454,809 A | 10/1995 | Janssen |
| 5,472,443 A | 12/1995 | Cordis et al. |
| 5,496,314 A | 3/1996 | Eggers |
| 5,549,604 A | 8/1996 | Sutcu et al. |
| 5,569,242 A | 10/1996 | Lax et al. |
| 5,599,346 A | 2/1997 | Edwards et al. |
| 5,647,871 A | 7/1997 | Levine et al. |
| 5,658,279 A | 8/1997 | Nardella et al. |
| 5,669,904 A | 9/1997 | Platt, Jr. et al. |
| 5,683,366 A | 11/1997 | Eggers et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,766,153 A | 6/1998 | Eggers et al. |
| 5,766,170 A | 6/1998 | Eggers |
| 5,785,704 A | 7/1998 | Bille et al. |
| 5,843,019 A | 12/1998 | Eggers et al. |
| 5,860,976 A | 1/1999 | Billings et al. |
| 5,873,855 A | 2/1999 | Eggers et al. |
| 5,891,095 A | 4/1999 | Eggers et al. |
| 5,891,142 A | 4/1999 | Eggers et al. |
| 5,919,189 A | 7/1999 | Benderev |
| 5,958,266 A | 9/1999 | Fugo et al. |
| 5,971,980 A | 10/1999 | Sherman |
| 6,004,319 A | 12/1999 | Goble et al. |
| 6,032,674 A | 3/2000 | Eggers et al. |
| 6,047,700 A | 4/2000 | Eggers et al. |
| 6,053,172 A | 4/2000 | Hovda et al. |
| 6,056,746 A | 5/2000 | Goble et al. |
| 6,059,782 A | 5/2000 | Novak et al. |
| 6,059,783 A | 5/2000 | Kirwan, Jr. |
| 6,066,134 A | 5/2000 | Eggers et al. |
| 6,066,137 A | 5/2000 | Greep |
| 6,102,046 A | 8/2000 | Weinstein et al. |
| 6,113,594 A | 9/2000 | Savage |
| 6,132,427 A | 10/2000 | Jones et al. |
| 6,135,988 A | 10/2000 | Turner et al. |
| 6,135,998 A | 10/2000 | Palanker |
| 6,149,620 A | 11/2000 | Baker et al. |
| 6,149,646 A | 11/2000 | West, Jr. et al. |
| 6,165,175 A * | 12/2000 | Wampler et al. ................ 606/48 |
| 6,183,469 B1 | 2/2001 | Thapliyal et al. |
| 6,190,381 B1 | 2/2001 | Olsen et al. |
| 6,210,404 B1 | 4/2001 | Shadduck |
| 6,228,081 B1 | 5/2001 | Goble |
| 6,228,082 B1 | 5/2001 | Baker et al. |
| 6,228,084 B1 | 5/2001 | Kirwan, Jr. |
| 6,254,600 B1 | 7/2001 | Willink et al. |
| 6,267,757 B1 | 7/2001 | Aita et al. |
| 6,287,305 B1 | 9/2001 | Heim et al. |
| 6,287,306 B1 | 9/2001 | Kroll et al. |
| 6,352,535 B1 | 3/2002 | Lewis et al. |
| 6,355,032 B1 | 3/2002 | Hovda et al. |
| 6,358,248 B1 | 3/2002 | Mulier et al. |
| 6,364,877 B1 | 4/2002 | Goble et al. |
| 6,398,779 B1 | 6/2002 | Buysse et al. |
| 6,447,511 B1 | 9/2002 | Slater |
| 6,458,121 B1 | 10/2002 | Rosenstock et al. |
| 6,478,794 B1 | 11/2002 | Trapp et al. |
| 6,479,785 B1 | 11/2002 | Fugo et al. |
| 6,482,201 B1 | 11/2002 | Olsen et al. |
| 6,482,205 B1 | 11/2002 | Bonnet et al. |
| 6,500,176 B1 | 12/2002 | Truckai et al. |
| 6,530,924 B1 | 3/2003 | Ellman et al. |
| 6,533,781 B2 | 3/2003 | Heim et al. |
| 6,544,261 B2 | 4/2003 | Ellsberry et al. |
| 6,589,237 B2 | 7/2003 | Woloszko et al. |
| 6,620,157 B1 | 9/2003 | Dabney et al. |
| 6,620,160 B2 | 9/2003 | Lewis et al. |
| 6,679,269 B2 | 1/2004 | Swanson |
| 6,726,683 B1 | 4/2004 | Shaw |
| 6,749,608 B2 | 6/2004 | Garito et al. |
| 6,770,071 B2 | 8/2004 | Woloszko et al. |
| 6,780,178 B2 * | 8/2004 | Palanker et al. ................ 606/34 |
| 6,787,730 B2 | 9/2004 | Coccio et al. |
| 6,802,842 B2 | 10/2004 | Ellman et al. |
| 6,818,102 B1 | 11/2004 | Viol |
| 6,837,887 B2 | 1/2005 | Woloszko et al. |
| 6,942,662 B2 * | 9/2005 | Goble et al. ...................... 606/48 |
| 6,949,096 B2 | 9/2005 | Davison et al. |
| 6,960,204 B2 | 11/2005 | Eggers et al. |
| 6,991,631 B2 | 1/2006 | Woloszko et al. |
| 7,004,941 B2 | 2/2006 | Tvinnereim et al. |
| 7,090,672 B2 | 8/2006 | Underwood et al. |
| 7,094,215 B2 | 8/2006 | Davison et al. |
| RE39,358 E | 10/2006 | Goble |
| 7,115,139 B2 | 10/2006 | McClurken et al. |
| 7,131,969 B1 | 11/2006 | Hovda et al. |
| 7,169,143 B2 | 1/2007 | Eggers et al. |
| 7,179,255 B2 | 2/2007 | Lettice et al. |
| 7,182,762 B2 | 2/2007 | Bortkiewicz |
| 7,186,234 B2 | 3/2007 | Dahla et al. |
| 7,192,428 B2 | 3/2007 | Eggers et al. |
| 7,195,627 B2 | 3/2007 | Amoah et al. |
| 7,195,630 B2 | 3/2007 | Ciarrocca |
| 7,201,750 B1 | 4/2007 | Eggers et al. |
| 7,238,185 B2 | 7/2007 | Palanker et al. |
| 7,270,658 B2 | 9/2007 | Woloszko et al. |
| 7,270,661 B2 | 9/2007 | Dahla et al. |
| 7,276,063 B2 | 10/2007 | Davison et al. |
| 7,357,802 B2 | 4/2008 | Palanker et al. |
| 7,429,262 B2 | 9/2008 | Woloszko et al. |
| 7,435,247 B2 | 10/2008 | Woloszko et al. |
| 7,445,618 B2 | 11/2008 | Eggers et al. |
| 7,468,059 B2 | 12/2008 | Eggers et al. |
| 7,736,361 B2 | 6/2010 | Palanker et al. |
| 7,789,879 B2 | 9/2010 | Palanker et al. |
| 2001/0012934 A1 | 8/2001 | Chandrasekaran et al. |
| 2001/0025177 A1 | 9/2001 | Woloszko et al. |
| 2001/0034519 A1 | 10/2001 | Goble et al. |
| 2002/0026186 A1 | 2/2002 | Woloszko et al. |
| 2002/0052599 A1 | 5/2002 | Goble et al. |
| 2002/0052600 A1 | 5/2002 | Davison et al. |
| 2003/0069573 A1 | 4/2003 | Kadhiresan et al. |
| 2004/0049251 A1 | 3/2004 | Knowlton |
| 2004/0138654 A1 | 7/2004 | Goble |
| 2004/0162554 A1 | 8/2004 | Lee et al. |
| 2004/0199157 A1 | 10/2004 | Palanker et al. |
| 2004/0236321 A1 | 11/2004 | Palanker at al. |

| | | | | | | |
|---|---|---|---|---|---|---|
| 2004/0267254 A1 | 12/2004 | Manzo et al. | | EP | 1 079 746 B1 | 3/2001 |
| 2005/0021028 A1 | 1/2005 | Palanker et al. | | EP | 1 080 680 A1 | 3/2001 |
| 2005/0177150 A1 | 8/2005 | Amoah et al. | | EP | 1 080 694 A1 | 3/2001 |
| 2005/0220674 A1 | 10/2005 | Shafirstein et al. | | EP | 1 082 944 B1 | 3/2001 |
| 2005/0234439 A1 | 10/2005 | Underwood | | EP | 1 158 917 B1 | 12/2001 |
| 2005/0234446 A1 | 10/2005 | Van Wyk et al. | | EP | 1 174 093 A1 | 1/2002 |
| 2005/0288665 A1 | 12/2005 | Woloszko | | EP | 1 179 320 A2 | 2/2002 |
| 2006/0069386 A1 | 3/2006 | Dubnack et al | | EP | 1 179 320 A3 | 2/2002 |
| 2006/0155270 A1 | 7/2006 | Hancock et al. | | EP | 1 205 155 A1 | 5/2002 |
| 2006/0235450 A1* | 10/2006 | Kasahara et al. ............ 606/159 | | EP | 1 253 866 B1 | 11/2002 |
| 2006/0253117 A1 | 11/2006 | Hovda et al. | | EP | 1 257 220 B1 | 11/2002 |
| 2006/0259025 A1 | 11/2006 | Dahla | | EP | 1 287 788 A1 | 3/2003 |
| 2006/0259033 A1 | 11/2006 | Nesbitt | | EP | 1 330 201 B1 | 7/2003 |
| 2007/0112348 A1 | 5/2007 | Eggers et al. | | EP | 1 330 989 B1 | 7/2003 |
| 2007/0129715 A1 | 6/2007 | Eggers et al. | | EP | 1 344 498 B1 | 9/2003 |
| 2007/0149966 A1 | 6/2007 | Dahla et al. | | EP | 1 374 788 A1 | 1/2004 |
| 2007/0179497 A1 | 8/2007 | Eggers et al. | | EP | 1 407 719 A3 | 4/2004 |
| 2007/0239156 A1 | 10/2007 | Palanker et al. | | EP | 1 581 128 B1 | 10/2005 |
| 2008/0004621 A1 | 1/2008 | Dahla et al. | | EP | 1 599 146 B1 | 11/2005 |
| 2008/0015565 A1 | 1/2008 | Davison | | EP | 1 632 191 A3 | 3/2006 |
| 2008/0021447 A1 | 1/2008 | Davison | | EP | 1 637 087 A3 | 3/2006 |
| 2008/0027428 A1 | 1/2008 | Palanker et al. | | EP | 1 693 015 A2 | 8/2006 |
| 2008/0039832 A1 | 2/2008 | Palanker et al. | | EP | 1 782 741 A3 | 5/2007 |
| 2008/0119842 A1 | 5/2008 | Palanker et al. | | EP | 1 880 686 A2 | 1/2008 |
| 2008/0125774 A1 | 5/2008 | Palanker et al. | | JP | 2001-178740 A | 7/2001 |
| 2009/0306642 A1 | 12/2009 | Vankov | | WO | WO-96/39914 A1 | 12/1996 |
| | | | | WO | WO-97/23169 A1 | 7/1997 |
| | FOREIGN PATENT DOCUMENTS | | | WO | WO-97/27893 A1 | 8/1997 |
| EP | 0 517 244 A1 | 12/1992 | | WO | WO-97/48346 A1 | 12/1997 |
| EP | 0 672 841 A2 | 9/1995 | | WO | WO-98/03117 A1 | 1/1998 |
| EP | 0 672 841 A3 | 9/1995 | | WO | WO-98/03220 A1 | 1/1998 |
| EP | 0 672 841 B1 | 9/1995 | | WO | WO-98/19625 A2 | 5/1998 |
| EP | 0 694 290 B1 | 1/1996 | | WO | WO-98/19625 A3 | 5/1998 |
| EP | 0 697 841 B1 | 2/1996 | | WO | WO-98/56324 A1 | 12/1998 |
| EP | 0 697 841 B2 | 2/1996 | | WO | WO-99/03407 A1 | 1/1999 |
| EP | 0 708 618 B1 | 5/1996 | | WO | WO-99/03408 A1 | 1/1999 |
| EP | 0 754 437 A3 | 1/1997 | | WO | WO-99/03409 A1 | 1/1999 |
| EP | 0 754 437 B1 | 1/1997 | | WO | WO-99/09919 A1 | 3/1999 |
| EP | 0 754 437 B2 | 1/1997 | | WO | WO-99/16359 A1 | 4/1999 |
| EP | 0 771 176 B1 | 1/1997 | | WO | WO-99/16359 C1 | 4/1999 |
| EP | 0 771 176 B2 | 1/1997 | | WO | WO-99/20213 A1 | 4/1999 |
| EP | 0 820 249 B1 | 1/1998 | | WO | WO-99/30655 A1 | 6/1999 |
| EP | 0 833 593 B1 | 4/1998 | | WO | WO-99/32042 A1 | 7/1999 |
| EP | 0 833 593 B2 | 4/1998 | | WO | WO-99/40858 A1 | 8/1999 |
| EP | 0 837 647 B1 | 4/1998 | | WO | WO-99/49799 A1 | 10/1999 |
| EP | 0 858 295 B1 | 8/1998 | | WO | WO-00/09053 A1 | 2/2000 |
| EP | 0 865 256 B1 | 9/1998 | | WO | WO-00/09053 C1 | 2/2000 |
| EP | 0 869 742 B1 | 10/1998 | | WO | WO-00/41638 A1 | 7/2000 |
| EP | 0 873 089 B1 | 10/1998 | | WO | WO-00/54683 A1 | 9/2000 |
| EP | 0 882 430 A3 | 12/1998 | | WO | WO-00/62685 A1 | 10/2000 |
| EP | 0 882 430 B1 | 12/1998 | | WO | WO-00/62698 A1 | 10/2000 |
| EP | 0 886 493 A3 | 12/1998 | | WO | WO-00/62698 C1 | 10/2000 |
| EP | 0 886 493 B1 | 12/1998 | | WO | WO-00/71043 A1 | 10/2000 |
| EP | 0 887 046 B1 | 12/1998 | | WO | WO-01/35845 A1 | 5/2001 |
| EP | 0 923 907 A1 | 6/1999 | | WO | WO-01/60273 A1 | 8/2001 |
| EP | 0 949 886 B1 | 10/1999 | | WO | WO-01/95819 A1 | 12/2001 |
| EP | 0 959 784 B1 | 12/1999 | | WO | WO-02/11635 A1 | 2/2002 |
| EP | 0 959 786 B1 | 12/1999 | | WO | WO-02/19932 A1 | 3/2002 |
| EP | 0 959 787 B1 | 12/1999 | | WO | WO-03/092521 A1 | 11/2002 |
| EP | 0 996 378 B1 | 5/2000 | | WO | WO-02/102255 A1 | 12/2002 |
| EP | 1 018 994 B1 | 7/2000 | | WO | WO-03/005882 A2 | 1/2003 |
| EP | 1 025 807 A3 | 8/2000 | | WO | WO-03/005882 A3 | 1/2003 |
| EP | 1 025 807 B1 | 8/2000 | | WO | WO-03/024305 A2 | 3/2003 |
| EP | 1 026 996 B1 | 8/2000 | | WO | WO-03/024305 A3 | 3/2003 |
| EP | 1 027 020 B1 | 8/2000 | | WO | WO-03/024339 A1 | 3/2003 |
| EP | 1 034 746 A3 | 9/2000 | | WO | WO-03/028542 A2 | 4/2003 |
| EP | 1 034 746 B1 | 9/2000 | | WO | WO-03/028542 A3 | 4/2003 |
| EP | 1 034 747 A1 | 9/2000 | | WO | WO-03/068311 A2 | 8/2003 |
| EP | 1 034 748 A1 | 9/2000 | | WO | WO-03/068311 A3 | 8/2003 |
| EP | 1 036 547 A2 | 9/2000 | | WO | WO-03/090638 A1 | 11/2003 |
| EP | 1 036 547 A3 | 9/2000 | | WO | WO-2004/002293 A2 | 1/2004 |
| EP | 1 039 862 B1 | 10/2000 | | WO | WO-2004/002293 A3 | 1/2004 |
| EP | 1 041 933 B1 | 10/2000 | | WO | WO-2004/022155 A2 | 3/2004 |
| EP | 1 050 278 A1 | 11/2000 | | WO | WO-2004/022155 A3 | 3/2004 |
| EP | 1 053 719 A1 | 11/2000 | | WO | WO-2004/071278 A2 | 8/2004 |
| EP | 1 053 720 A1 | 11/2000 | | WO | WO-2004-071278 A3 | 8/2004 |
| EP | 1 055 399 A1 | 11/2000 | | WO | WO-2004/073752 A2 | 9/2004 |
| EP | 1 061 857 B1 | 12/2000 | | WO | WO-2004/112581 A2 | 12/2004 |
| EP | 1 065 981 B1 | 1/2001 | | WO | WO-2004/112581 A3 | 12/2004 |

| WO | WO-2005/009213 | A2 | 2/2005 |
| --- | --- | --- | --- |
| WO | WO-2005/009213 | A3 | 2/2005 |
| WO | WO-2005/072634 | A2 | 8/2005 |
| WO | WO-2005/072634 | A3 | 8/2005 |
| WO | WO-2005/112806 | A2 | 12/2005 |
| WO | WO-2005/112806 | A3 | 12/2005 |
| WO | WO-2005/117735 | A1 | 12/2005 |
| WO | WO-2005/122936 | A1 | 12/2005 |
| WO | WO-2005/122938 | A1 | 12/2005 |
| WO | WO-2006/002337 | A2 | 1/2006 |
| WO | WO-2006/002337 | A3 | 1/2006 |
| WO | WO-2006/051252 | A1 | 5/2006 |
| WO | WO-2006/125007 | A2 | 11/2006 |
| WO | WO-2006/125007 | A3 | 11/2006 |
| WO | WO-2007/103800 | A2 | 9/2007 |
| WO | WO-2007/103800 | A3 | 9/2007 |
| WO | WO-2007/103800 | C1 | 9/2007 |
| WO | WO-2007/143445 | A2 | 12/2007 |
| WO | WO-2007/143445 | A3 | 12/2007 |

OTHER PUBLICATIONS

Extend European Search Report mailed on May 24, 2011, for EP Application No. 07861654.7, filed on Nov. 1, 2007, eight pages.

International Search Report and Written Opinion mailed on May 15, 2008, for PCT Application PCT/US2007/023130, filed on Nov. 1, 2007, six pages.

U.S. Appl. No. 11/787,500, filed Apr. 16, 2007, by Palanker et al.

Cushing, H. (Dec. 1928). "Electro-Surgery as an Aid to the Removal of Intracranial Tumors," *Surgery, Gynecology and Obstetrics*, XLVII(6):751-784.

European Examination Report mailed on Dec. 12, 2008, for EP Application No. 04755740.0 filed on Jun. 18, 2004, four pages.

European Search Report mailed on Jul. 18, 2007, for EP Application No. 04755740.0 filed on Jun. 18, 2004, four pages.

International Preliminary Report on Patentability mailed on Oct. 15, 2009, for PCT Application No. PCT/US2008/004460, filed on Apr. 4, 2008, six pages.

International Search Report mailed on Dec. 8, 2005, for PCT Application No. PCT/US04/19785, filed on Jun. 18, 2004, one page.

Jones, H.M. et al. (Jan. 15, 1995). "Pulsed Dielectric Breakdown of Pressurized Water and Salt Solutions," *J. Appl. Phys.* 77(2):795-805.

Jones, H.M. et al. (Jan. 14, 1995). "Development of Pulsed Dielectric Breakdown in Liquids," *J. Phys. D: Appl. Phys.* 28(1):178-188.

Miller, J.M. et al. (Jun. 2003). "Precision and Safety of the Pulsed Electron Avalanche Knife in Vitreoretinal Surgery," *Arch Opthalmol* 121:871-877.

Mylrea, K.C. et al. (Jul.-Sep. 1981). "Introduction to Electrosurgery," *Journal of Clinical Engineering* 6(3):185-191.

Palanker, D. et al. (Jun. 1, 1997). "Electrical Alternative to Pulsed Fiber-Delivered Lasers in Microsurgery," *J. Appl. Phys.* 81(11):7673-7680.

Palanker, D. et al. (2002). "Effect of the Probe Geometry on Dynamics of Cavitation," *Proc. SPIE* 4617:112-117.

Supplemental European Search Report mailed on Jul. 3, 2008, for EP Application No. 04 71 1134.9, filed on Sep. 14, 2005, five pages.

Written Opinion mailed on Dec. 8, 2005, for PCT Application No. PCT/US04/19785, filed on Jun. 18, 2004, three pages.

European Examination Report mailed on Sep. 2, 2010, for EP Application No. 03733930.6, filed on May 2, 2003, six pages.

Extended European Search Report mailed on Aug. 22, 2011, for EP Application No. 10175129.5, filed on Apr. 11, 2008, seven pages.

* cited by examiner

ELECTRIC PLASMA-MEDIATED CUTTING AND COAGULATION OF TISSUE AND SURGICAL APPARATUS

CROSS-REFERENCE TO RELATED APPLICATION

This application claims priority to U.S. Provisional Application No. 60/856,549 filed Nov. 2, 2006, title "Probe for Cutting Coagulation and Fulguration," inventors: Daniel V. Palanker, Paul O. Davison and Alexander B. Vankov, incorporated by reference here in its entirety.

FIELD OF THE INVENTION

This invention relates generally to surgical methods and apparatus and particularly to electrosurgery.

BACKGROUND

Plasma-mediated thermo-electric cutting for surgery is well known, see for instance, Palanker U.S. Pat. Nos. 6,135,988 and 6,780,178. See also Eggers et al. U.S. Pat. Nos. 6,047,700 and 5,697,882. These disclose plasma-mediated cutting of soft biological tissue where the tissue is immersed or profused with saline solution which, of course, is an electrically conductive medium. See also Palanker et al. U.S. Pat. No. 7,238,185 and McClurken et al. U.S. Pat. No. 7,115,139. For instance, Palanker et al. U.S. Pat. No. 7,238,185 discloses apparatus and method for cutting biological tissue where the tissue being cut is submerged in a conductive liquid medium. The cutting apparatus has a cutting electrode and a return electrode. Both electrodes are immersed in the conductive medium and a voltage (signal) applied between them in order to heat the medium, thus producing a vapor cavity around the cutting portion of the blade and ionizing a gas inside the vapor cavity to produce a plasma.

However, in actual surgical procedures such as carried out on people or animals, often the tissues are not immersed in a naturally occurring conductive medium such as blood or internal bodily fluids. Then typically a conductive medium such as saline solution is introduced as part of the surgical procedure ("wet field" electrosurgery). Typically the saline or other conductive medium is introduced onto or into the surgical field as part of the surgical procedure. The present inventors have recognized that this requirement to provide the conductive fluid is a drawback since in some cases fluid obscures the surgical field; it somewhat complicates the surgical procedure, and unless the conductive fluid is kept replenished it may cause a breakdown in the plasma regime, thus interfering with the cutting. Also, electric current flowing through the conductive fluid away from the tissue results in unnecessary power dissipation and associated increase in collateral tissue damage.

An additional technical problem is that electrosurgical equipment typically is used for three main classes of procedures. First, there is cutting of tissue. Next, there is coagulation (sealing) of blood vessels. Next, there is fulguration or ablation which is a species of coagulation typically involving somewhat different levels of heat application, but also for sealing or closing tissue. Some existing electrosurgical equipment provides all of these. However, the amount and type of electrical energy applied for each of these is different and all-purpose devices are generally somewhat unsatisfactory. Moreover, combining such functions in one device is problematic since the types of RF energy applied to achieve the plasma typically differ substantially for each of the three.

SUMMARY

Disclosed here is a method suitable for plasma-mediated electro-thermal cutting of tissue where the tissue to be cut is not bathed or submerged in an electrically conductive medium. In one embodiment, the electrosurgery takes place with the tissue being cut or coagulated while being in contact with a low conductive liquid supplied during the surgical procedure (not natural bodily fluids), meaning a liquid which is a relatively poor conductor of electricity. (This does not refer to its thermo-conductive properties which differ from the electro-conductive properties.) As well known, generally bodily fluids such as blood, bile and other internal bodily fluids such as in joints are high in dissolved salts or other ions and hence relatively electrically conductive. For purposes of this disclosure such fluids are considered conductive since they will typically sustain an electric current at relatively low voltages. A low conductive liquid in this sense includes, for instance, water, glycine, oils, mixtures of water and non-ionic compounds and various other liquids or semi-liquids well known in the field. While these are inherently thermally conductive (as are all fluids), their electro-conductive properties are poor and in an electrical sense they are more insulators than conductors. The provision here of such a liquid or semi-liquid which is of low conductivity has the advantage that it provides local convective and conductive cooling. Cooling is useful here since the applied RF signal and resulting plasma typically cause a considerable elevation in temperature of the adjacent tissue being operated on. This may result in local burning or charring of the tissue which is undesirable.

Thus the present method for cutting or otherwise operating on (e.g., coagulating) tissue generally includes the steps of contacting the tissue with a plasma generating electrode wherein the electrode is at least partially surrounded by a low conductive fluid supplied from a source external to the body, and applying an electric signal, having in some cases a low duty-cycle, to the electrode that is in contact with the low conductive fluid. The signal causes the formation of a plasma along the electrode between the electrode and the tissue and this plasma performs the tissue cutting or other operation.

As used here, the term low conductive fluid includes liquids and semi-liquids and semi-solids such as gels and suspensions. A typical such fluid is pure water and others such as glycine, either in its pure form or mixed with water. Other suitable liquids are ocular visoelastic fluid, perfluorocarbons and other oils. Other mixtures of water and non-ionic compounds also result in a low conductive fluid. Generally low conductivity here refers to a resistivity above 1,000 ohm-cm. As well known, electrical resistance is equal to resistivity× length÷area. Resistivity is typically expressed in units of Ohm·meter or Ohm·cm. Hence low conductive fluid here includes not only distilled or deionized water, but also water or other liquids that may contain very small amounts of ions or otherwise are very slightly conductive so their conductivity is at least an order of magnitude less than that of natural bodily liquids.

The electrode here used with the cooling fluid may be any one of the well known electro-surgery types or other types. A particular type is disclosed here but this is not limiting. Other types are disclosed in the above referenced patents, and also see U.S. Patent Application Publication No. 2004/0199157, inventor Daniel V. Palanker, incorporated herein by reference in its entirety, disclosing yet another electrode. The electrode typically defines an edge. The edge, however, is not like that of an ordinary knife which does the cutting solely via mechanical application to the tissue being cut. Instead here the edge of the electrode focuses for the electric field induced by the applied electrical signal. This field concentrated at the edge generates a local plasma discharge. Hence the edge may be tapered or flat or sharp, but need not be of any particular dimensions or level of sharpness. In some cases the edge itself may be relatively dull. The tissue cutting may be assisted by mechanical force supplied by the edge of the electrode, as in conventional cutting. Moreover, the electrode conventionally may be configured as a monopolar or bipolar cutting tool in terms of the electrode arrangement. A return electrode (in close proximity to the primary electrode) or a grounding pad (for the monopolar arrangement) is provided spaced apart from the primary electrode to serve as a current return path. The return electrode is typically placed as a pad on tissue having contact with the tissue being cut, or in conductive liquid having such contact.

In general here, the plasma is formed along the edge of the electrode by application of an electrical signal to the electrode. To further decrease the heat accumulation and associated collateral tissue damage, low duty cycle waveforms are used. As well known, duty-cycle refers to the proportion of time that the energy is actually being applied. Low duty-cycle here typically refers to duty-cycles of less than 10% which may be, for instance, 1% or less, or 0.1% or less. In some cases the low duty-cycle refers to the pulse voltage regime that is applied to the electrode. For instance, a pulsed low duty-cycle signal may include a plurality of pulse bursts that are separated by more than one millisecond (e.g., has a frequency of less than 1 KHz) where each burst is shorter than one millisecond. The burst of pulses may include pulses that are biphasic (e.g., of alternating polarity) and the pulses may have different peak voltages. Again, none of this is limiting. The low duty-cycle is intended to minimize tissue charring or burning.

Note that the presence of the low conductive fluid here has little or no effect on the plasma generation or the cutting or other capabilities of the apparatus. Thus tissue may be cut or otherwise affected by the plasma when the electrode is initially dry, that is, surrounded by for instance ambient air only, and continue to be cut as the blade (electrode edge) becomes immersed in the low conductive fluid and also natural conductive fluid such as blood. Hence for the present method to be operative there is no need for the electrode edge to be fully immersed in the low conductive fluid during the entire time of cutting or coagulation or ablation. Since the purpose of the fluid here is cooling, as long as enough fluid is provided for sufficient time to remove heat as desired, that is adequate. For instance, when skin is cut to begin a surgical procedure, there may be no need to initially supply the low conductive fluid which may be introduced into the wound only after the skin has been penetrated.

Another advantage of immersion in a non-conductive fluid is that electric current is concentrated in the area of contact of the electrode with tissue. If the electrode is held in a conductive fluid, current will flow not only through the tissue but also through the fluid around it, and thus more heat will be deposited at the site. In addition, if the electrode is held in air above the tissue, dielectric breakdown (plasma arc) can occur between the electrode and tissue in multiple location along the electrode surface, connecting the electrode with the tissue and resulting in energy dissipation at the locations of contact of the arcs with tissue. Since the threshold of dielectric breakdown in liquids in much higher than in the air, the addition of a non-conductive fluid will prevent arcing in the areas other than at locations of the direct contact of electrode with tissue. This will result in much better localization of the energy deposition into the tissue, leading to reduced collateral damage.

Also provided here is a method of electrosurgical dry field tissue cutting, whereby human or animal skin tissue is cut (resected) without application thereto of any conductive or non-conductive fluid. Note that skin is essentially devoid of conductive natural bodily fluids such as blood, etc. and so is by its nature a dry field. This method is accomplished by application of a relatively low power electrical signal to the cutting electrode which cuts the skin (both epidermis and dermis) cleanly, without charring or burning.

Also disclosed here is an electrosurgery apparatus, also referred to in the field as a cutting head, which includes a first portion intended for the coagulation (or fulguration or ablation) function and a second portion intended for the tissue cutting function. These portions are combined so that the two portions are each associated with an electrode at the terminus of the cutting head. The two electrodes are spaced quite close together but isolated electrically. The operator (surgeon) selects at any one time whether he wishes to cut or coagulate. The associated electrode is then energized with a suitable electrical signal (typically of different frequency duty-cycle, etc.) for each function. The two electrodes are each optimized for their intended function in terms of their configuration. The two electrodes, while located closely adjacent one another, are separated by insulating (dielectric) material.

Moreover, in one embodiment each electrode is provided with a suitable band pass filter to prevent cross talk or feedback of the RF signal applied to each electrode from propagating in the other of the electrodes. In one embodiment the coagulation electrode is a C-shaped structure, that is, having a curved shape, and is superimposed on a rounded edge which defines part of the cutting edge for the cutting electrode function. The two electrodes are electrically insulated from one another by a dielectric material and fastened together by, for instance, epoxy material. The separation between them is enough to prevent arcing there between. In one embodiment two such coagulation electrodes are provided, driven by the same RF signal and with one being located on each side of the cutting electrode to provide even coagulation on each side of the cut.

In another embodiment, a single component electrode blade performs cutting and coagulation. The exposed blade edge is used for cutting. The blade flat part is used for coagulation. The flat part is mostly electrically insulated, but the insulation defines a plurality of through holes, partly exposing the underlying flat part of the blade.

DETAILED DESCRIPTION

Electrosurgery with Cooling Fluid

Figures 1A, 1B:
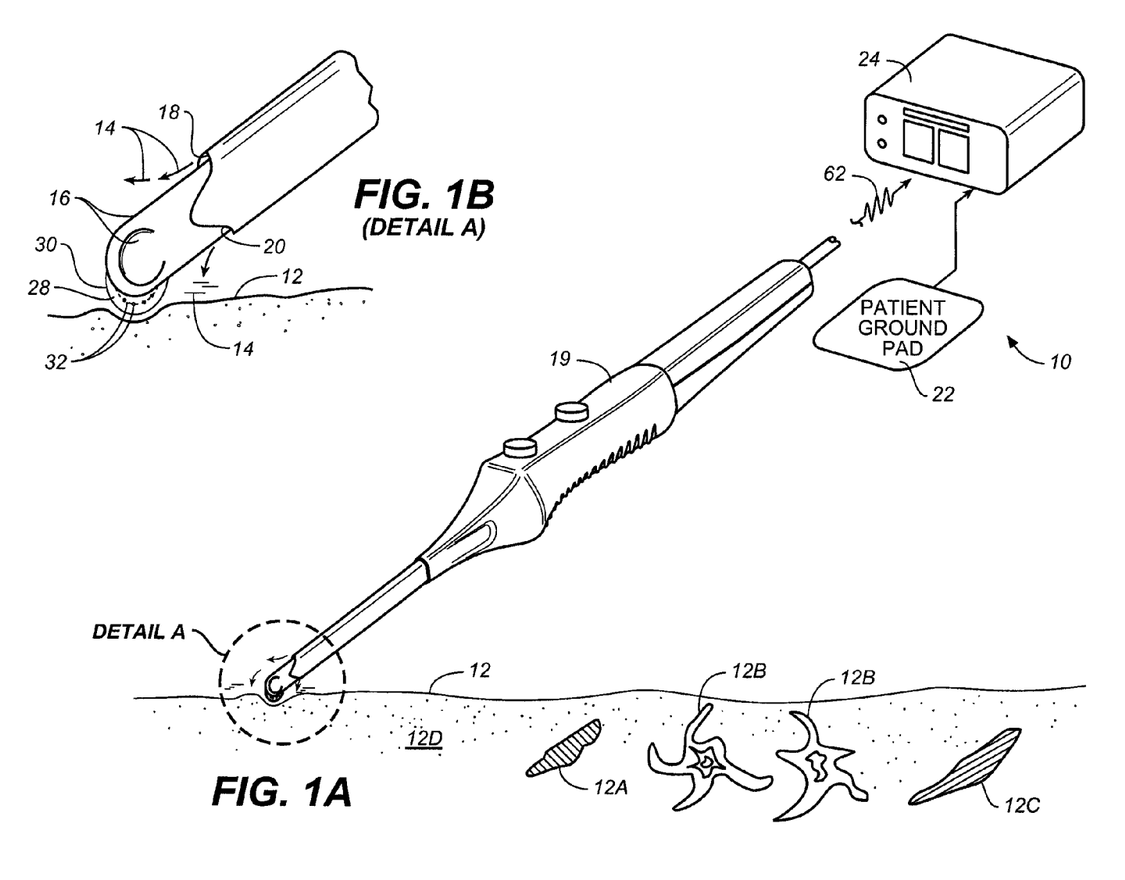
FIGS. 1A, 1B show a method for electrosurgery using a low conductive fluid.

FIG. 1A, which bears some similarity to FIG. 1 of U.S. Pat. No. 7,238,185, shows an apparatus 10 for cutting material 12 submerged in a low conductivity liquid medium 14. FIG. 1B shows detail of FIG. 1A, enlarged. Note that in U.S. Pat. No. 7,238,185 this medium 14 is expressly described as being a conducting liquid medium and the electrode generates the plasma in the conducting liquid medium. That is a difference between present FIG. 1B and FIG. 1 of U.S. Pat. No. 7,238,185 since in present FIG. 1 the plasma is generated in the tissue being operated on, and the electrode is in effect in contact with the tissue in order to generate the plasma. Material 12 is biological tissues including, for instance, muscle tissue 12A, nerve tissue 12B, bone 12C and connective tissue 12D.

Apparatus 10 includes handpiece 19 terminating in cutting electrode 16. Suitable material for the electrode 16 for instance would be tungsten, titanium, molybdenum, stainless steel or alloys thereof. Again, this is not limiting. The cutting electrode 16 is surrounded by insulating layer 20. A return electrical path is provided by conventional patient grounding pad 22. Insulating layer 20 can be any suitable dielectric material. Fluid 14 is supplied via handpiece 19 at 18, 20 which define an outlet near electrode 16. Fluid 14 may alternatively by supplied via a separate tubing or conduit, not part of handpiece 19, in any case from an external reservoir.

Also provided is a voltage control unit 24 also known as a radio frequency (RF) generator which provides the electrical (radio frequency in this case) signals which energize the apparatus via lead or leads 62. In this case unit 24 has a pulse control for pulsing the voltage in accordance with a predetermined modulation format, see U.S. Pat. No. 7,238,185 incorporated herein by reference.

In this case a thin layer of a plasma 28 is formed around the cutting blade 16. Thus electrode 16 is immersed in the low conductive fluid 14 and put in contact with tissue 12 and a suitable RF signal applied to electrode 16, such that tissue 12 is heated to produce a vapor cavity region 30 around the blade 16 adjacent to the tissue. Vapor cavity region 30 is thereby filled with water vapor and other gasses 32 emanating from the tissue 12 during the vaporization. The layer of gas 32 is ionized in the strong electric field around the cutting electrode 16 to make a thin layer of plasma 28.

The actual nature of the applied electrical signals which are suitable to create the desired plasma effect is well known in the field. For instance, in one case the applied signal is an RF (radio frequency) signal having a frequency in the range of 100 KHz to 10 MHz. Typically this energy is applied in the form of bursts of pulses. Each burst typically has a duration in the range of 10 microseconds to 1 millisecond. The individual pulses in each burst typically each have a duration of 0.1 to 10 microseconds with an interval therebetween of 0.1 to 10 microseconds. The actual pulses are typically square waves and bi-phasic, that is alternating positive and negative amplitudes. Generally the interval between pulses must be shorter than a lifetime of the plasma vapor cavity in order to maintain the cavity and the plasma regime during each pulse burst. In one embodiment the bursts each are separated by a duration of at least one millisecond. Typically the time between the pulse bursts is sufficient so that the duty-cycle is relatively low as explained above. This minimizes the undesirable heating effects. However, as indicated here the provision of the cooling fluid reduces heating problems also. Typically the plasma has a temperature greater than 100° C.

Combination Cutting and Coagulation Apparatus

Figure 2:
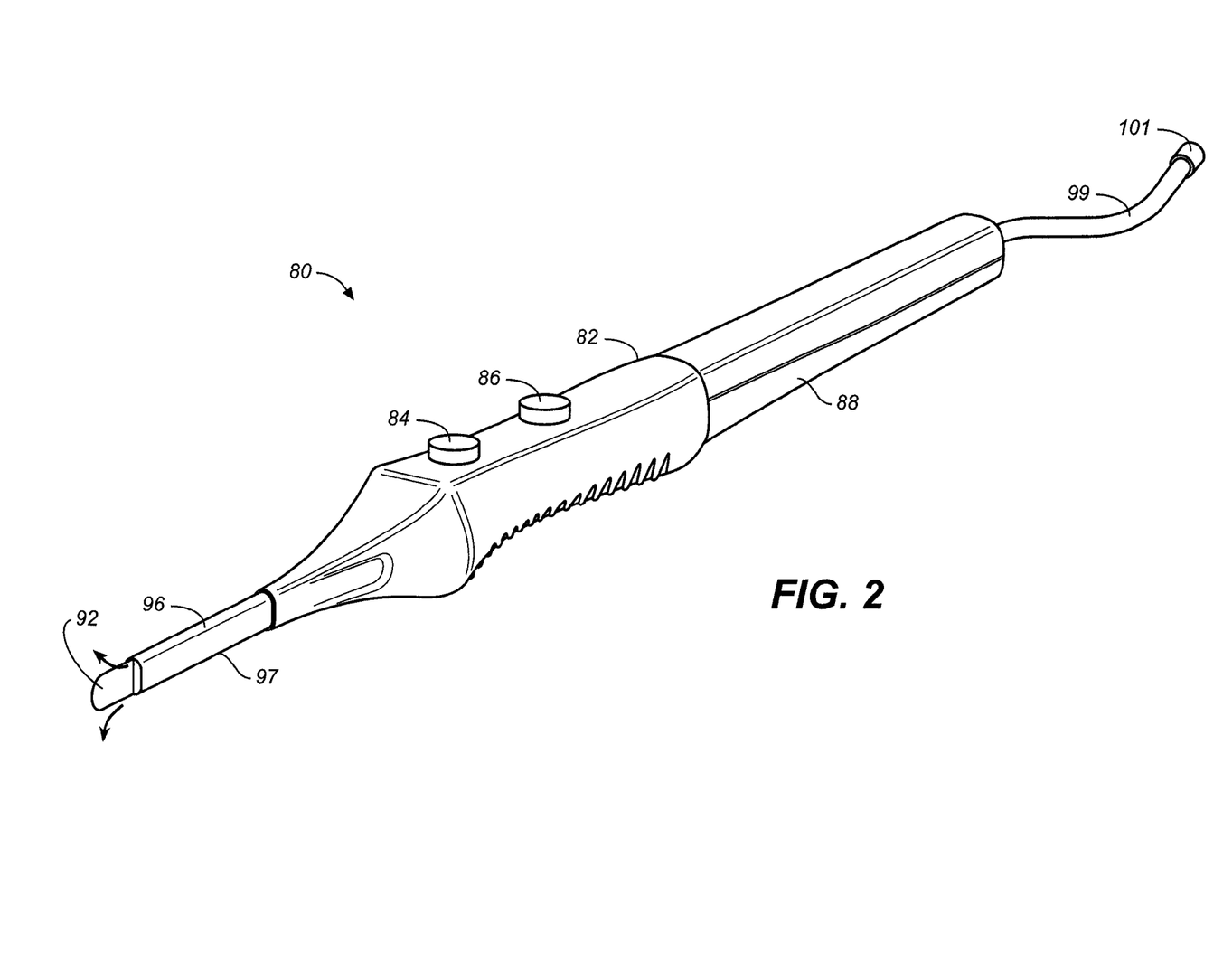
FIG. 2 shows an overview of a hand piece of an electrosurgery apparatus for a dual function head as described herein.

The following discloses a new electrode configuration intended for a combination cutting and coagulation and fulguration and ablation, shown also in FIG. 1A but not required for the method of FIG. 1A. An overview of the hand piece 80 (corresponding to handpiece 19 in FIG. 1A) is shown in FIG. 2 for the present such combination device. This figure omits the pulse generator 24 and associated electrical lead or leads 62 shown in FIG. 1A, which are provided for the FIG. 2 apparatus but not shown here for simplicity. The FIG. 2 device 80 is mostly conventional in configuration except as disclosed further herein. It includes a hand grip portion 82 with hand grip ridges as shown on the lower part thereof. This portion is intended to be held in the surgeon's hand. Two control buttons 84, 86 activate electric switches (not shown) which are provided for purposes of respectively selecting the cutting or coagulation regimes. Note that the ablation function can also be carried out, in the cutting regime, by a sweeping of the cutting electrode over the region to be ablated. The rear portion 88 is for balance and for holding the electrical leads extending there from which terminate in a conventional electrical connector (not shown) which connects to lead (or leads) 62 to the generator 24 (also not shown in FIG. 2). The dimensions of the device of FIG. 2 are such that it is comfortably held in a hand, yet small enough for surgery for the intended application. The working end of the device of FIG. 2 includes at its distal end the electrode tip assembly 92, described below with reference to FIG. 3. Assembly 92 is attached to the body portion 82 by an intermediate portion (shaft) 96. The intermediate portion 96 carries the electrical leads to the tip assembly 92 as described with reference to FIG. 3. In a typical situation, the entire assembly 80 is disposable and is disposed of after each surgery. Of course, this disposable aspect is not limiting. The materials for the device of FIG. 2 are conventional and the portions shown are typically molded from plastic with the exception of the electrical leads and electrode tip assembly 92, whose configuration is described further below.

Figure 3:
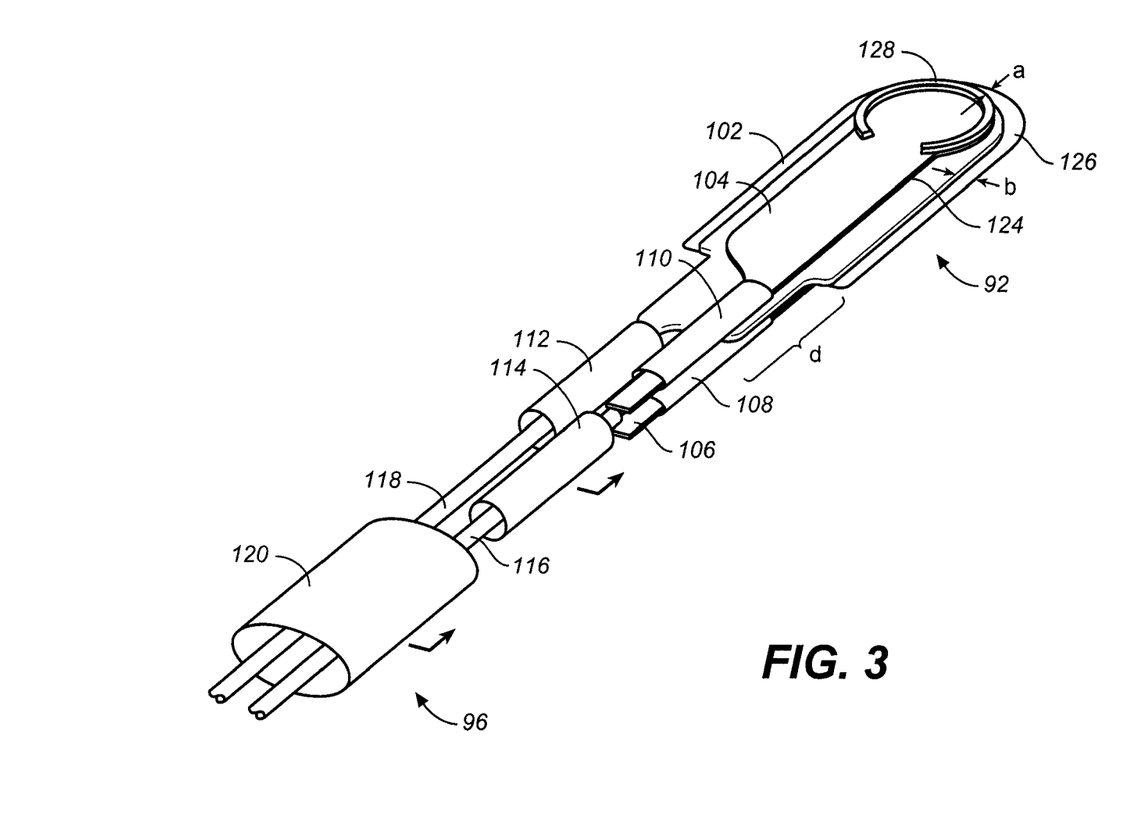
FIG. 3 shows detail of the structure of the FIG. 2 device.

FIG. 3 shows in a perspective view detail of the electrode tip assembly 92 and the nearest part of the intermediate portion 96. FIG. 3 is a semi-exploded view as described hereinafter. In FIG. 3, the cutting blade subassembly (electrode) 102 includes the actual cutting electrode. Associated therewith and fixed thereto is the left side coagulation electrode subassembly 104 and the right side coagulation electrode subassembly 106 (mostly not visible). Electrical insulation, which is plastic heat shrink tubing 108 and 110, is provided for electrodes 104 and 106. Also provided are lengths of heat shrink plastic tubing 112 and 114. As indicated by the arrow associated with insulation 114, this piece of tubing is meant to be slid forward during assembly of this device. (It is shown in the retracted view merely for purposes of illustration.)

The RF energizing signals are provided to the three electrodes 102, 104, 106 by respectively a length of wire 116 and a second length of wire 118. In one embodiment, these are 30 gauge insulated wire. The three electrodes are adhered together by an epoxy adhesive layer indicated at 124. (A similar epoxy layer, not visible, adheres electrode 106 to electrode 102.) A length of large diameter plastic heat shrink tubing 120 is provided and slides forward as indicated by the arrow during the assembly of the device at the factory. This is intended to be slid all the way forward to cover the other pieces of insulating tubing at location d. Dimensions a and b are respectively 0.030 inches (0.75 mm) and 0.02 inches (0.5 mm). Of course these dimensions are merely illustrative. These dimensions define the distance between the edge of the cutting electrode 102 and the coagulation electrodes 104, 106. Note that the right hand side (lower) coagulation electrode subassembly 106 is mostly not visible in FIG. 3 because it is on the bottom side of the apparatus 92. Hence in this particular embodiment, there are two coagulation electrodes, one on the top which is mostly visible at 104, and a second only partly visible at 106. This allows even coagulation on both sides of the cut. These same two coagulation electrodes each perform fulguration, at a different power setting than used for coagulation.

Not shown in FIG. 3 is the coaxial tubing 97 for fluid delivery of FIG. 2, which fits around coaxially the left most (rear) part of tubing 120. The terminus of tubing 97 defines the opening portion 18,20 of FIG. 1B which delivers the cooling fluid 14 to the area being operated on. In another embodiment, tubing 97 is omitted since the FIG. 3 apparatus does not require the cooling fluid, or cooling fluid may be delivered by other means. Also, tubing 97 may be used to deliver conductive fluid, such as saline solution, depending on the intended use by the surgeon.

Figures 4A, 4B:
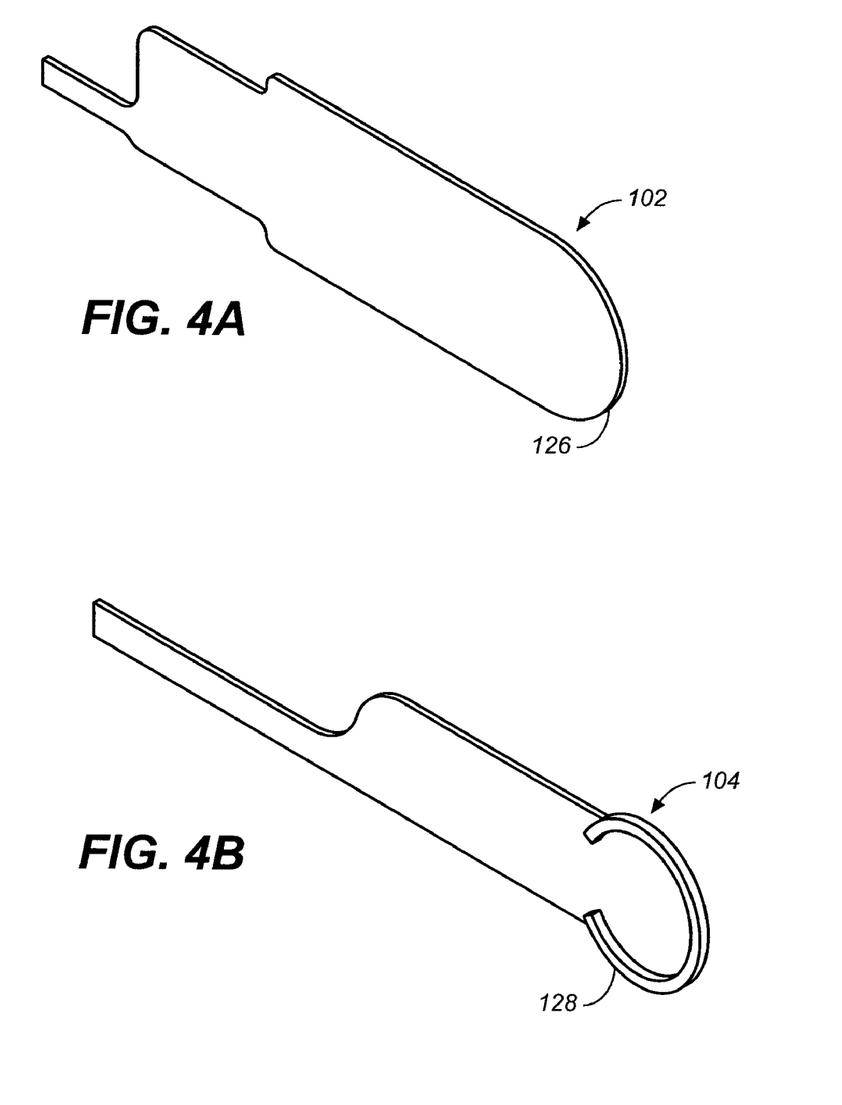
FIGS. 4A and 4B, respectively, show detail of the present cutting electrode and coagulation electrodes.

FIGS. 4A and 4B respectively show perspective views of part of the cutting blade subassembly 102 and the left side (upper) coagulation electrode subassembly 104. The right side (lower) coagulation electrode subassembly 106 is essentially a mirror image of the FIG. 4B component. The cutting blade subassembly 102 of FIG. 3 is relatively simple. In this embodiment it includes a support piece of annealed sheet titanium 0.1 mm thick as shown in FIG. 4A, to which is spot welded a slightly wider cutting blade of approximately similar shape and made of stainless steel (or titanium) sheet which is 0.01 inch (0.25 mm) thick. The actual edge 126 thereof is honed to a sharp edge tapered at e.g. 10° on one side only. A number of each of these components is typically conventionally machined, stamped, or etched out of a large sheet of metal. In one embodiment, the entire structure 102 is approximately 0.61 inches (15 mm) long and its width is 0.217 inches (5.5 mm). The rounded edge 126 here is, e.g., a section of a circle (not limiting).

The coagulation electrode subassembly 104 of FIG. 4B is more complicated since it exhibits three dimensionally as shown in the FIG. 4B perspective view. The active (exposed) portion of the electrode is the C-shaped section 128, which as shown is slightly raised. In one embodiment, the C-shaped section has an overall thickness of 0.008 inches (0.2 mm) and the raised portion is 0.004 inches (0.1 mm) thick. The open part of the C-shaped section subtends approximately a 60° arc. The total length of the FIG. 4B structure in one embodiment is 0.681 inches (17.3 mm). Again this component is typically one of many etched or stamped or machined out of a large sheet of, e.g., titanium, which has been annealed for hardness. The overall diameter of the C-shaped section in one embodiment is approximately 0.138 inches (3.5 mm). The other coagulation electrode 106 is essentially similar but a mirror image, since it lies on the other side of the cutting electrode.

With reference to FIG. 3, not shown is an overall glass or other electric insulating layer covering most of the structure but leaving the C-shaped section of electrode 104 (and electrode 106) exposed and also leaving exposed the actual edge 126 of the cutting blade portion 102. Moreover there is similar insulation (dielectric) provided between each of cutting blade subassembly 102 and the two coagulation electrodes 104, 106. This typically again is a coating of glass or ceramic approximately 0.005 to 0.5 mm thick, preferably 0.01 to 0.2 mm thick. The insulation extends to the proximal portion of each electrode. The glass type insulation is typically applied by a conventional process of dipping each relevant component prior to assembly in liquid (molten) glass and then annealing the glass. In FIG. 3, wire 116 provides the RF signal for the coagulation function and is spot welded or otherwise attached to the proximal terminal (and uninsulated) portions of both coagulation electrodes 104 and 106. The other wire 118 similarly attaches to the terminal proximal portion of cutting blade subassembly 102.

Further with regard to FIG. 3, in general the exposed C-shaped surface area of each of the coagulation electrodes 104, 106 is much larger than that of the exposed cutting edge 126 of electrode 102, since most of the cutting blade assembly 102 (except its edge) is covered by the insulation material so that typically only the actual edge 126 is exposed and this lies more or less flush with the surrounding insulating material. The width of the exposed edge 126 is in the range of 0.01 to 0.1 mm. The larger exposed surface area of the coagulation electrodes 104, 106 makes coagulation of large tissue surfaces or blood vessels easier due to the extended area of contact and increased application of electrical power. To prevent electrical arc between the cutting and coagulation electrodes potentially leading to electrode damage, sufficient spacing between the electrodes is provided. In general, the less the distance between electrodes, the more arcing, therefore it is desirable to maintain a certain minimum spacing between cutting and coagulation electrodes as provided by the FIG. 3 configuration.

Further, the particular electrode configuration as shown in FIG. 3 is not limiting. For instance in one embodiment, the cutting electrode instead of being a relatively large plate, mostly covered by insulation, is instead a length of wire partially embedded in an insulating body with a portion of the wire exposed. An exposed edge of a plate is equivalent in terms of plasma generation to a wire. Again this wire is separated from the coagulation electrode by a suitable minimum distance along its length to prevent arcing.

In these figures the return electrode is not shown since it is typically a separate grounding pad structure or equivalent of conventional type as in FIG. 1A, not necessarily part of the cutting/coagulation hand piece 80. However, that is not limiting.

Note moreover that the apparatus of FIG. 3 does not show how it would be used in conjunction with the introduction of the low conductivity liquid into the operating field. In one embodiment, the liquid is introduced into the surgical field by a separate length of tubing, not part of the FIG. 2 or FIG. 3 structures. In other embodiments a tubing or conduit is incorporated or defined in the hand piece 80 of FIG. 2 with its distal end connected to a reservoir of suitable liquid and terminating near the working end of the FIG. 3 structure, such as in the vicinity of the electrode assembly 92. The surgeon conventionally controls the rate of liquid delivery (e.g., 10 to 200 ml/min) through the tubing or conduit.

The fluid delivery aspect is thereby illustrated in FIG. 2, where tubing 97 is coaxial with intermediate portion 96. The arrows illustrate the fluid flow from tubing 97. At the distal end of the rear portion 88 is connected tubing 99 for the fluid, connecting to valve 101 and hence to a fluid reservoir such as a bag of pure water (not shown). Tubing 99 connects to tubing 97 via a conduit extending through hand piece 80. Typically coaxial tubing 97 terminates 10 to 20 mm from the end of intermediate portion 96.

Figure 4C:
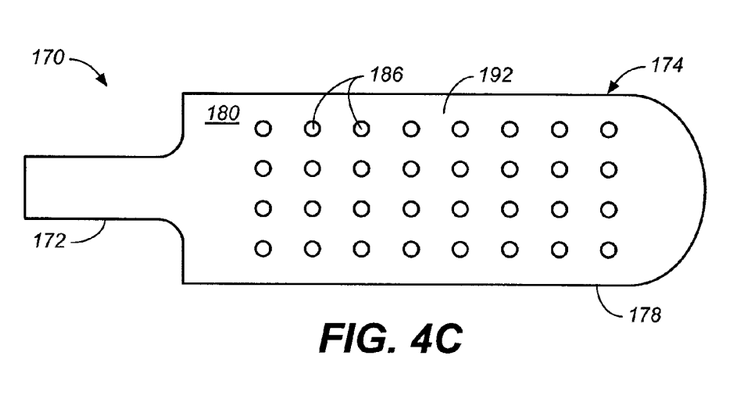
FIGS. 4C and 4D show another version of a dual function electrode structure.

FIG. 4C shows another type of combination cutting and coagulation electrode 170, but having a single blade used for both functions. Hence this is an alternative to and corresponds in terms of function to the dual electrode structure of FIGS. 3 and 4A and 4B, but is simpler in construction. FIG. 4C only illustrates the blade, not the electrical leads or hand piece which would be similar to that of FIG. 2. Note that only one electrical lead would be needed with the FIG. 4C electrode. FIG. 4C shows this electrode in a plan view. It includes a base or rear portion 172 for attachment of the electrical lead. The working portion 174 has about the same overall length, width and thickness and edge configuration as structure 102 in FIG. 4A, and is of a similar material, and is similarly electrically insulated, except for edge 178, by an overlayer of e.g. glass electrical insulation 180.

Figure 4D:
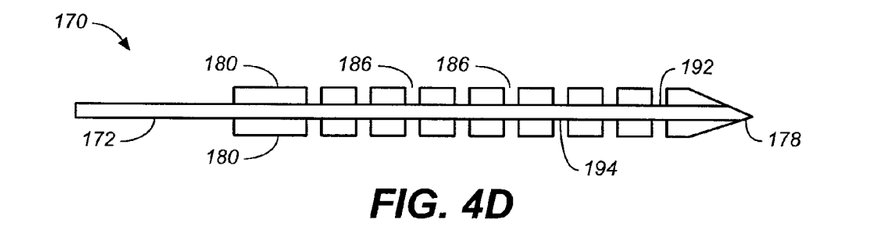

Electrical insulation layer 180 defines a number (e.g., 10 to 100) of openings 186 which each expose the underlying metal of the blade portion 174. The openings 186 are more or less evenly spaced apart and are each in the range of 1 to 100 µm in diameter, preferably 10 to 50 µm. The glass insulation layer 180 is e.g. 0.05 to 0.25 mm thick. As shown in side cross sectional view in FIG. 4D (not to scale), electrode 170 has the insulating layer 180 on both its flat sides 192, 194 both sides also defining openings 186. Note that in FIG. 4D the blade edge is shown as being tapered; the tapering is somewhat exaggerated for purposes of illustration in this figure.

In use, the electrode edge 178 is used for cutting, and the flat sides 192, 194 with the penetrated insulation layer 180, for coagulation, similar to use of the FIG. 3 electrodes. The surgeon chooses coagulation or cutting at any one time, by activating the appropriate controls such as buttons 84,86 in FIG. 2 so as to supply suitable pulsed energy to the electrode 170.

Figure 5:
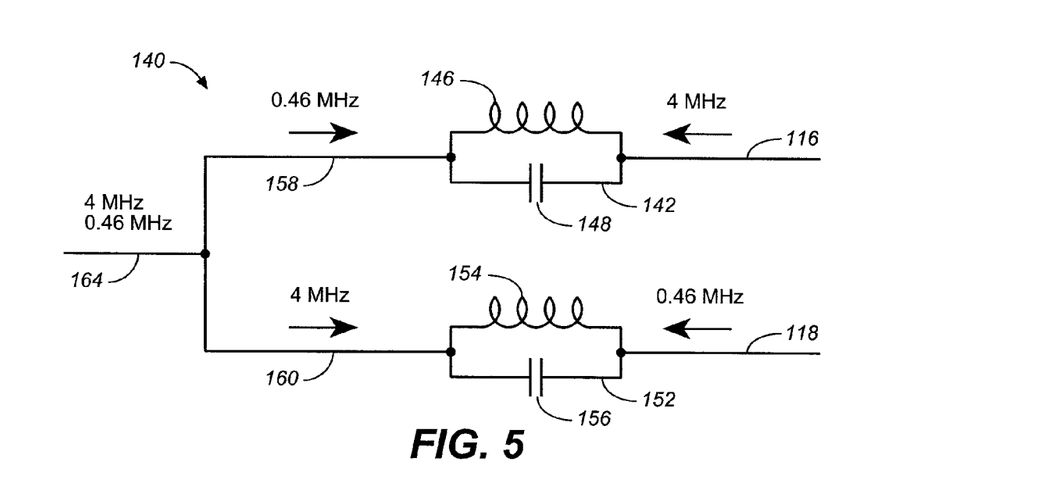
FIG. 5 shows a schematic diagram of a circuit for filtering of the electrical signals applied to the FIG. 2 device.

FIG. 5 shows an electrical circuit 140 in schematic form, which typically is provided in the handle portion 82 of the hand piece 80 of FIG. 2 on a suitable circuit board for use with the FIG. 3 dual electrode. This circuit has two arms. The upper arm is coupled to wire (lead) 116, which in turn connects to the two coagulation electrodes 104 and 106 (not shown). The lower arm is coupled to the second wire (lead) 118, which connects to the cutting blade subassembly (electrode) 102. The upper arm of FIG. 5 includes a band pass filter 142, including an inductance 146 and a capacitance 148. However this is merely representative of any sort of band pass (or band stop) filter. The bottom portion includes a different value band pass filter 152, including in this case inductor 154 and capacitor 156, again not meant to be limiting but merely to illustrate a band pass (or band stop) filter.

In this embodiment, two different electrical signals are provided as is conventional, one for coagulation and the second for cutting as controlled by hand piece 80 buttons 84, 86 or a foot switch (not shown). Typically coagulation uses a lower frequency RF signal than does cutting. In this case as illustrated, the coagulation RF signal applied to lead 158 is at a frequency of 0.46 MHz. (The other characteristics of this signal are not indicated here since this is merely an indication of the nature of this signal.) As indicated by the arrow, this signal is intended propagate to the coagulation electrodes 104, 106. An RF signal of different 4 MHz frequency is applied to lead 160 which is not necessarily connected to lead 158 and this 4 MHz signal is intended to connect to the cutting blade electrode 102. The source of both these RF signals is the RF generator unit 24 shown in FIG. 1.

The present inventors have recognized the technical problem that the cutting electrode 102 here lies in close proximity to an arc source (electrodes 104, 106) useful for large scale coagulation which may lead to breakdown of the gap between the electrodes 102 and 104 or 106, especially when a wet cutting head is partially exposed to air. Breakdown of this gap, e.g., shorting, may cause damage to the delicate cutting electrode and may also result in damage to the power supply unit 24. Even if the cutting electrode 102 is connected to ground to protect the RF generator 24, an arc between the coagulation electrodes 104, 106 and cutting electrode 102 may destroy either electrode when a high voltage bipolar waveform is used as the energizing signal. Even when electrically floating, electrodes can still conduct enough current through cable (lead) capacitance in order to damage the cutting edge of the cutting electrode 102, which is quite thin.

Therefore to reduce cross talk between the cutting and coagulation energizing signals, two different frequencies are used here for cutting and coagulation as in FIG. 5. The band pass filters 142, 152 provided as shown in FIG. 5 isolate the two signals. As illustrated this prevents the cross talk of the 4 MHz frequency signal from propagating back up into the upper arm of FIG. 5. Similarly filter 152 prevents the coagulation signal of 0.46 MHz frequency, even though picked up in wire 118, from propagating to the lower arm. Band stop filters can be used instead of band pass filters if the energizing frequencies are shifted far enough from one another for complete isolation.

In this way both the coagulation and cutting electrodes may be supplied with their signals from the same RF generator 24 and in some cases may even be supplied by the same output line from the generator 24. In this case a common node 164 is provided as shown in FIG. 5 to which both the cutting and coagulation RF signals at respectively 4 MHz and 0.46 MHz are applied. The filters 142, 152 prevent the undesired signal from propagating down to the respective wires 116 and 118 in each arm of the circuit of FIG. 5. In other embodiments the common node 164 is not present, and separate signals are provided to lines 158 and 160 from the RF generator unit 24.

Dry Field Skin Tissue Cutting

Also disclosed here is a method of cutting (resecting) skin tissue including the epidermis (outer layer) and dermis (under layer) using an electrosurgery electrode in a dry field environment. "Dry field" here refers to the absence of naturally occurring conductive bodily fluids and the absence of a conductive fluid applied to skin (such as saline solution). Note that the epidermis by definition is free of blood vessels. The underlying dermis does have some blood vessels, but the blood supply is limited since the blood vessels are small. In the surgical field, it is conventional that to cut skin electrosurgically a conductive fluid is needed to prevent tissue charring. Generally therefore skin is cut using a conventional scalpel. This is because the use of the added conductive fluid is difficult since the fluid tends to not remain alongside the electrode and thereby maintenance of the plasma regime along the electrode is problematic.

In accordance with the present invention, dry skin or skin with only a non-conductive fluid in it or on it is cut using an electrosurgical electrode of conventional configuration or as described above. The pulsed electrical energy applied to the electrode is controlled to be of relatively low power (much lower than is conventional in electrosurgery), so no skin charring occurs. Typically the amount of peak electrical power is at least 100 Watts, and the duty cycle of the electrical signal is 15% or less.

With regard to the nature of the relatively low power also see e.g. copending and commonly owned and published U.S. application Ser. No. 10/779,529, filed Feb. 13, 2004, inventor Daniel Palanker, incorporated herein by reference in its entirety, and also the above disclosure of suitable energization of the electrode. For instance, the signal applied to the electrode is in one case an RF signal having a frequency in the range of 100 KHz to 10 MHz. Typically this energy is applied in the form of bursts of pulses. Each burst typically has a duration in the range of 10 microseconds to 1 millisecond. The individual pulses in each burst typically have a duration of 0.1 to 10 microseconds, with an interval therebetween of 0.1 to 10 microseconds, as above. Typically the pulse bursts each are separated by a duration of at least 1 millisecond, thereby providing the low duty cycle. This minimizes the heating effects.

This relatively low power signal maintains the desired plasma regime, and allows for tissue cooling between bursts. Thus it allows for cutting the human epidermis and dermis with minimal charring. Generally any resulting tissue damage is no more than that resulting from cutting skin with a conventional (non-electrosurgery) scalpel. The resulting wound therefore would heal as quickly as a wound created by a conventional scalpel. This approach has the advantage of allowing the surgeon to use the same electrosurgical apparatus for skin cutting as for surgery within the body. It also allows for cutting and coagulation using the same instrument.

This disclosure is illustrative but not limiting; further modifications will be apparent to those skilled in the art in light of this disclosure and are intended to fall within the scope of the appended claims.

What is claimed:

1. Apparatus for electrosurgery, adapted to be coupled to first and second electrical leads, comprising:
    a first monopolar electrode adapted for tissue coagulation together with a remote return electrode and to be coupled to the first lead, the first electrode defining at its extremity a curved shape, a closed part of the curved shape being distal from the first lead;
    a second monopolar electrode adapted for tissue cutting together with the remote return electrode and to be coupled to the second lead, the second electrode having an elongated shape terminating at its extremity in a curved portion;
    the first electrode lying over the second electrode and being electrically insulated therefrom to prevent a current from flowing therebetween; and
    an electrically insulating layer partially covering the second electrode and at least partly exposing an edge of the second electrode.

2. The apparatus of claim 1, wherein the insulating layer is glass or ceramic.

3. The apparatus of claim 1, wherein each of the electrodes is substantially of titanium or stainless steel.

4. The apparatus of claim 1, wherein a thickness of the edge of the second electrode is in the range of 0.01 mm to 0.20 mm.

5. The apparatus of claim 1, wherein all of the curved shape of the first electrode is spaced apart from an adjacent part of the second electrode by a distance in the range of 0.25 mm to 5.0 mm.

6. The apparatus of claim 1, further comprising a third monopolar electrode adapted for tissue coagulation together with the remote return electrode and to be coupled to the first lead, and lying over a surface of the second electrode opposed to the first electrode, and being electrically insulated from the second electrode.

7. The apparatus of claim 1, wherein a thickness of insulation between the first and second electrodes is in the range of 0.01 to 0.2 mm.

* * * * *